United States Patent
Bruzinski et al.

(10) Patent No.: US 9,102,698 B2
(45) Date of Patent: Aug. 11, 2015

(54) PROCESS FOR THE SYNTHESIS OF IB-MECA

(75) Inventors: Paul Bruzinski, Clifton Park, NY (US); Xuejun Liu, Arcadia, CA (US); Cameron Gibb, Delmar, NY (US); Pedro E. HErnandez-Abad, Arroyo, PR (US)

(73) Assignee: CAN-FITE BIOPHARMA LTD., Petach Tikva (IL)

( * ) Notice: Subject to any disclaimer, the term of this patent is extended or adjusted under 35 U.S.C. 154(b) by 826 days.

(21) Appl. No.: 12/450,094

(22) PCT Filed: Mar. 13, 2008

(86) PCT No.: PCT/IL2008/000360
§ 371 (c)(1),
(2), (4) Date: Sep. 11, 2009

(87) PCT Pub. No.: WO2008/111082
PCT Pub. Date: Sep. 18, 2008

(65) Prior Publication Data
US 2010/0087636 A1    Apr. 8, 2010

Related U.S. Application Data

(60) Provisional application No. 60/906,838, filed on Mar. 14, 2007.

(51) Int. Cl.
*C07H 19/16* (2006.01)
*C07H 1/00* (2006.01)

(52) U.S. Cl.
CPC . *C07H 19/16* (2013.01); *C07H 1/00* (2013.01)

(58) Field of Classification Search
CPC .................................. C07H 1/00; C07H 19/16
See application file for complete search history.

(56) References Cited

U.S. PATENT DOCUMENTS

| | | | |
|---|---|---|---|
| 5,773,423 A | 6/1998 | Jacobson et al. | |
| 2006/0014944 A1 | 1/2006 | Takahashi et al. | |
| 2007/0099865 A1 | 5/2007 | Fishman et al. | |

FOREIGN PATENT DOCUMENTS

| | | |
|---|---|---|
| GB | 1385830 A | 3/1975 |
| JP | 49-30392 A | 3/1974 |
| JP | 49-66695 A | 6/1974 |
| WO | 95/02604 A1 | 1/1995 |
| WO | 00/40251 A1 | 7/2000 |
| WO | 02/055085 A2 | 7/2002 |
| WO | 2004/038419 A1 | 5/2004 |
| WO | 2004/045627 A1 | 6/2004 |
| WO | 2005/011053 A1 | 2/2005 |
| WO | 2005/063246 A1 | 7/2005 |
| WO | 2006/011130 A1 | 2/2006 |
| WO | 2006/048884 A1 | 5/2006 |
| WO | 2006/059328 A1 | 6/2006 |
| WO | 2007/063538 A1 | 6/2007 |
| WO | 2007/086044 A1 | 8/2007 |

OTHER PUBLICATIONS

"1,4-Dioxane", Novolyte Technologies Product Data Sheet; last viewed Feb. 9, 2012.*
Cappellacci, L. et al., Journal of Medicinal Chemistry, "Synthesis, Biological Evaluation, and Molecular Modeling of Ribose-Modified Adenosine Analogues as Adenosine Receptor Agonists", 2005, vol. 48, pp. 1550-1562.*
Greene, T. W., Protective Groups in Organic Synthesis, Third Edition, Copyright 1999; Chapter 2: Protection for the Hydroxyl Group, Including 1,2- and 1,3-Diols; pp. 17-23 and 207-215.*
Joshi, B. V. et al., Current Topics in Medicinal Chemistry, "Purine Derivatives as Ligands for A3 Adenosine Receptors", 2005, vol. 5, pp. 1275-1295.*
Gao, Z.-G. et al., Bioorganic & Medicinal Chemistry Letters, "Conversion of A3 adenosine receptor agonists into selective antagonists by modification of the 5'-ribofuran-uronamide moiety", 2006, vol. 16, pp. 596-601.*
The Whyte Group of Companies, "Hunig's base", last modified Apr. 2001, also available at http://www.hunigs.com/.*
Afify, H. M. N. M., et al., "A Novel and Facile Reaction to N6-Alkylated Adenosine via Benzotriazole as a Synthetic Auxiliary", J. Heterocyclic Chem., vol. 37, pp. 339-341, (2000).
Bar-Yehuda, S., et al., "Agonists to the A3 adenosine receptor induce G-CSF production via NF-κB activation: A new class of myeloprotective agents", Experimental Hematology, vol. 30, pp. 1390-1398, (2002), Elsevier Science Inc.
Devine, S. M., et al., "An efficient convergent synthesis of adenosine-5'-N-alkyluronamides", Tetrahedron, vol. 64, pp. 1772-1777, (2008), Elsevier Ltd.
Fishman, P., et al., "Evidence for involvement of Wnt signaling pathway in IB-MECA mediated suppression of melanoma cells", Oncogene, vol. 21, pp. 4060-4064, (2002), Nature Publishing Group.
Fishman, P., et al., "Targeting the A3 Adenosine Receptor for Cancer Therapy: Inhibition of Prostate Carcinoma Cell Growth by A3AR Agonist", Anticancer Research, vol. 23, pp. 2077-2084, (2003).

(Continued)

*Primary Examiner* — Layla Bland
*Assistant Examiner* — Bahar Craigo
(74) *Attorney, Agent, or Firm* — Vorys, Sater, Seymour and Pease LLP; Susanne M. Hopkins

(57) ABSTRACT

The present disclosure provides a method for the synthesis of IB-MECA. More specifically, the present disclosure provides a simple and high yield method for Good Manufacturing Production (GMP) of IB-MECA. The method involves the reaction of 6-halopurine-9-riboside with a diol protecting reagent; oxidation of the primary alcohol in the diol protected 6-halopurine-9-riboside with a diol protecting reagent; oxidation of the primary alcohol in the diol protected 6-halopurine; reaction of the diol protected 6-halopurine with a nucleophile (e.g. methylamine); substitution of the halogen group with iodobenzylamine and removal of the diol protecting group.

13 Claims, No Drawings

(56) References Cited

OTHER PUBLICATIONS

Gallo-Rodriguez, C., et al., "Structure-Activity Relationships of N6-Benzyladenosine-5'-uronamides as A3- Selective Adenosine Agonists", J. Med. Chem., vol. 37, pp. 636-646, (1994).

Linden, J., "Reviews: Cloned adenosine A3 receptors: pharmacological properties, species differences and receptor functions", TiPS, vol. 15, pp. 298-306, (1994), Elsevier Science Ltd.

Merighi, S., et al., "Pharmacological and biochemical characterization of adenosine receptors in the human malignant melanoma A375 cell line", British Journal of Pharmacology, vol. 134, pp. 1215-1226, (2001), Nature Publishing Group.

Poulsen, S-A., et al., "Review Article: Adenosine Receptors: New Opportunities for Future Drugs", Bioorganic & Medicinal Chemistry, vol. 6, pp. 619-641, (1998), Elsevier Science Ltd.

Rodenko, B., et al., "Solid phase synthesis and antiprotozoal evaluation of di- and trisubstituted 5'-carboxamidoadenosine analogues", Bioorganic & Medicinal Chemistry, vol. 14, pp. 1618-1629, (2006), Elsevier Ltd.

DeNinno, et al., "3'Aminoadenosine-5'-uronamides: Discovery of the First Highly Selective Agonist at the Human Adenosine A3 Receptor", J. Med. Chem., vol. 46, pp. 353-355, (2003).

DeNinno, et al., "The synthesis of highly potent, selective, and water-soluble agonists at the human adenosine A3 receptor", Bioorganic & Medicinal Chemistry Letters, vol. 16, pp. 2525-2527, (2006).

Rodenko, et al., "Solid phase synthesis and antiprotozoal evaluation of di- and trisubstituted 5'-carboxamidoadenosine analogues", Bioorganic & Medicinal Chemistry, vol. 14, pp. 1618-1629, (2006).

Jeong, et al., "Design and synthesis of 3'-ureidoadenosine-5'-uronamides: effects of the 3'-ureido group on binding to the A3 adenosine receptor", Bioorganic & Medicinal Chemistry Letters, vol. 14, pp. 4851-4854, (2004).

Siddiqi, et al., "Search for New Purine- and Ribose-Modified Adenosine Analogues as Selective Agonists and Antagonists at Adenosine Receptors", J. Med. Chem., vol. 38, pp. 1174-1188, (1995).

* cited by examiner

PROCESS FOR THE SYNTHESIS OF IB-MECA

This is a National Phase Application filed under 35 U.S.C. 371 as a national stage of PCT/IL2008/000360, filed on Mar. 13, 2008, an application claiming the benefit under 35 U.S.C. 119(e) U.S. Provisional Application No. 60/906,838, filed on Mar. 14, 2007, the entire content of each of which is hereby incorporated by reference in its entirety.

FIELD OF THE INVENTION

This invention is in the field of chemistry and in particular relates to the synthesis of an $A_3$ adenosine receptor agonist.

BACKGROUND OF THE INVENTION

Adenosine is a ubiquitous purine nucleoside which is secreted extra-cellularly by metabolically active and stressed cells. Adenosine is an important regulatory molecule through its binding to at least 4 G-protein-associated cell surface receptors, currently classified $A_1$, $A_{2a}$, $A_{2b}$ and $A_3$ [Linden B. *TiPS* 15: 298-306 (1994); Poulsen S, *Bioorg Med Chem* 6: 619-41 (1998)].

Almost all human tissues express adenosine receptors of 1 or more classes, and this includes, in high density, various tumor cells [Merighi S, et al. *Br. J. Pharmacol.* 134: 1215-1226 (2001)]. $A_1$ and $A_3$ receptor activation causes G-protein signal transduction leading to reduced activity of kinases PKB/Akt and PKA, and decreased formation of cAMP; this inhibits cell growth [Fishman P, et al. *Oncogene* 21: 4060-4064 (2002)].

1-deoxy-1-(6-{[(3-iodophenyl)methyl]amino}9H-purine-9-yl)-N-methyl-β-d-ribofuranuronamide (methyl 1-[N6-(3-iodobenzyl)-adenin-9-yl]-β-D-ibofuronamide, IB-MECA; MW=510.29 Da) is an orally active adenosine receptor agonist with specific, submicromolar potency at the $A_3$ receptor ($K_i$=0.47M).

In vivo, orally administered IB-MECA inhibits the development of tumors in syngeneic (melanoma, colon carcinoma) and xenograft (colon and prostate carcinoma) mouse models [Fishman P. et al. *Anticancer Res.* 23(3A): 2077-2083 (2003)].

It has also been found that giving IB-MECA orally to mice stimulates the production of neutrophils via an increase in granulocyte colony stimulating factor (G-CSF) and, correspondingly, IB-MECA protects against cytotoxic-induced myelo-toxicity [Bar-Yehuda S, et al. *Exp. Hematol.* 30: 1390-139 (2002)]. Oral IB-MECA also inhibits progression of colon carcinoma in nude mice, and stimulates neutrophil recovery after cytotoxic drug therapy in this strain.

Considerable evidence has been accumulated indicating that adenosine through its receptors play also an important role in limiting inflammation. Adenosine's anti-inflammatory effects are manifested by inhibition of TNF-α, interleukin-1 and interleukin-6 production. The involvement of adenosine in mediating the effect of several anti-inflammatory drugs such as aspirin, methotrexate and sulfasalazin has been described, supporting the role of adenosine in the regulation of the inflammatory process. Recent studies suggested that the highly selective $A_3$ adenosine receptor ($A_3$AR) agonist IB-MECA inhibited the production of TNF-α and MIP-1α in vitro while preventing the development of collagen and adjuvant induced arthritis (AIA) in experimental animal models (WO2004/045627). In addition, it has been shown that $A_3$AR is highly expressed in synovial and peripheral blood mononuclear cells (PBMNC) of AIA rats and its level down regulates upon IB-MECA treatment (WO 2004/038419).

The chemical synthesis of adenosine $A_3$ receptor selective agonists, particularly adenine compounds, among others, the IB-MECA, was first described by Jacobson K. et al. in U.S. Pat. No. 5,773,423.

US Patent application publication No. 2006/0014944 describes a method for the synthesis of nucleotides.

SUMMARY OF THE INVENTION

According to the first of its aspects, the invention provides a method for the chemical synthesis of IB-MECA, having the following formula (I):

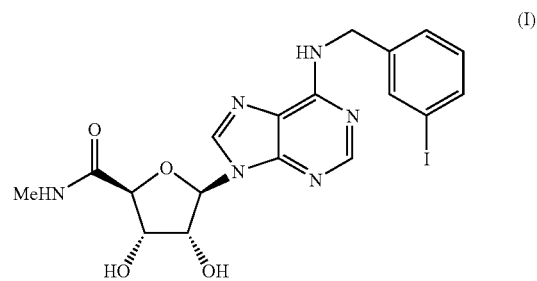 [SMILES: CNC(=O)[C@H]1O[C@@H](n2cnc3c(NCc4cccc(I)c4)ncnc32)[C@H](O)[C@@H]1O]

(I)

The method in accordance with the invention comprises:
(i) reacting 6-halopurine-9-riboside of the following formula (II):

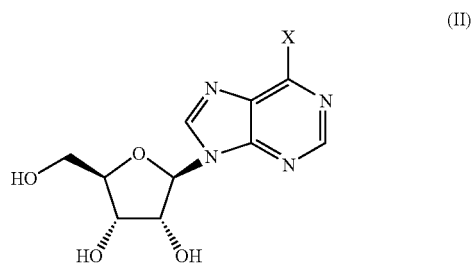

(II)

wherein X is a halogen selected from Cl, I or Br;
with a diol protecting reagent to obtain a diol protected 6-halopurine of the following formula (III):

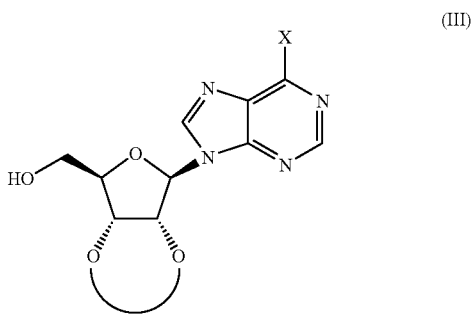

(III)

wherein said diol protecting reagent comprises a straight or branched $C_1$-$C_6$ alkyl group;

(ii) oxidizing the primary alcohol in said diol protected 6-halopurine of formula (III) to a respective carboxylic acid derivative of formula (IV):

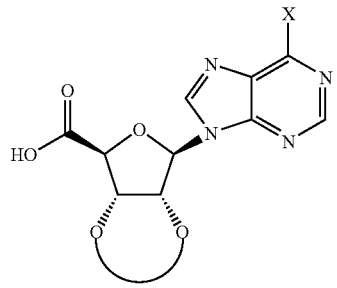

(iii) reacting the carboxylic acid group of the derivative of formula (IV), with a methylamine to obtain the respective methylamide derivative of the diol protected 6-halopurine (III), the methylamide derivative having the formula (V):

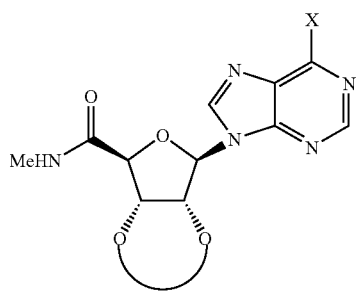

(iv) substituting the halogen group of said methylamide derivative (V) with 3-iodobenzylamine to form a diol protected IB-MECA having the formula (VI);

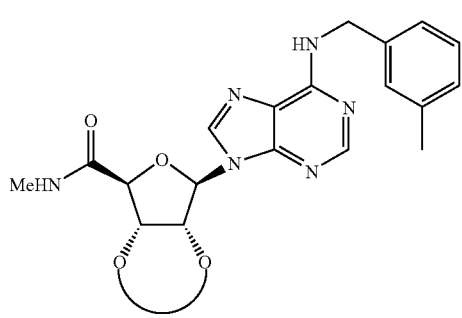

(v) removing the diol protection to obtain said IB-MECA of formula (I).

The invention also provides chemically synthesized IB-MECA whenever obtained by the method of the invention as well as pharmaceutical compositions comprising the said chemically synthesized IB-MECA.

DETAILED DESCRIPTION OF SOME EXEMPLARY EMBODIMENTS

The present invention is based on the development of an efficient method for the synthesis of IB-MECA, and the finding that this method is also suitable for current good manufacturing production (cGMP) of IB-MECA. It is noted that IB-MECA is referred to at times by the term CF101.

Thus, there is disclosed herein a method for the chemical synthesis of IB-MECA, having the following formula (I):

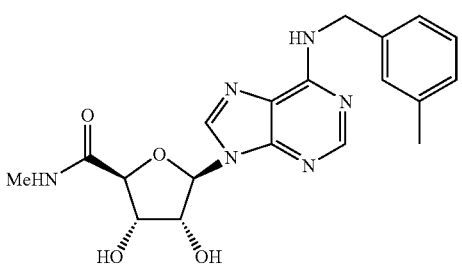

the method comprising:

(i) reacting 6-halopurine-9-riboside of the following formula (II):

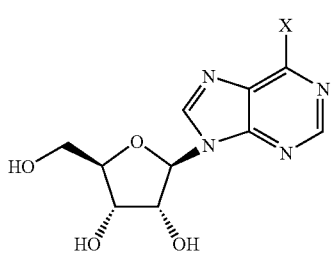

wherein X is a halogen selected from Cl, I or Br;

with a diol protecting reagent to obtain a diol protected 6-halopurine of the following formula (III):

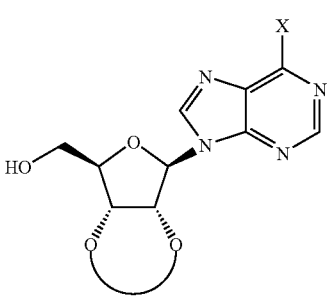

wherein said diol protecting reagent comprises a straight or branched $C_1$-$C_6$ alkyl group;

(ii) oxidizing the primary alcohol in said diol protected 6-halopurine of formula (III) to a respective carboxyl derivative of formula (IV):

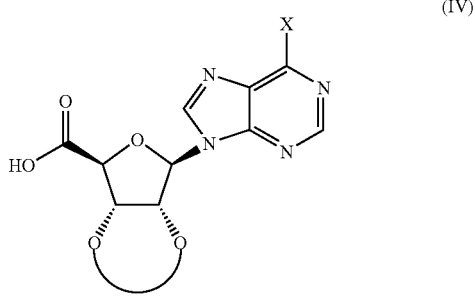

(iii) reacting the carboxylic acid group of the derivative of formula (IV) with a methylamine to obtain the respective methylamide derivative of the diol protected 6-halopurine (III), the methylamide derivative having the formula (V):

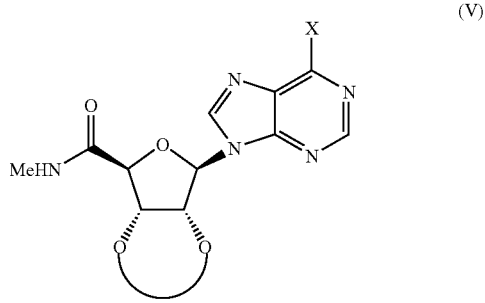

(iv) substituting the halogen group of methylamide derivative (V) with 3-iodobenzylamine to form a diol protected IB-MECA having the formula (VI); and

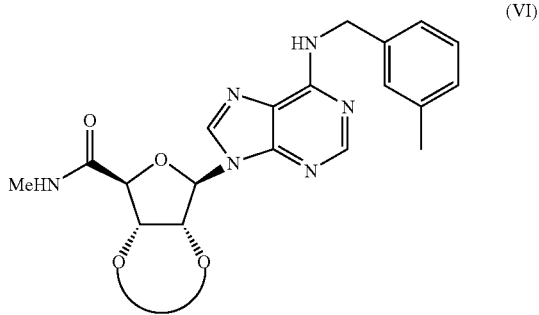 [SMILES: CNC(=O)[C@H]1O[C@@H](n2cnc3c(NCc4cccc(C)c4)ncnc32)[C@H](O)[C@@H]1O]

(v) removing diol protection to obtain said IB-MECA of formula (I).

In the present disclosure, the term "protecting reagent" is used to denote any chemical moiety which is introduced into a molecule by chemical modification of a functional group in order to obtain chemoselectivity in a subsequent chemical reaction. A variety of protecting reagents are known to those versed in the art of organic chemistry. As used herein, the protecting reagent reacts with a functional group(s) a substrate molecule to form a protected substrate. This protected substrate is stable to reaction conditions to which the protected substrate will be subjected after which it is removable from a protected substrate to liberate the functional group(s) under conditions that are compatible with other functionality present in the substrate. The hydroxyl groups of 1,2-diols may be individually protected or may be jointly protected with a cyclic diol protecting group. Examples of suitable hydroxyl protecting groups and diol protecting groups may be found in T. W. Greene et al. "*Protective Groups in Organic Synthesis*", 3rd Ed., John Wiley and c Sons Inc., NY (1999), which is incorporated herein by reference.

In accordance with the present disclosure the protecting reagent comprises a $C_1$-$C_6$ alkyl moiety. In one embodiment disclosed herein, the protection of the diol funtional group is achieved when reacting a molecule comprising said diol group with a protecting reagent, for example, and without being limited thereto, with $C_3$-$C_6$ dialkyloxyalkane, thereby forming a protective cyclic acetal moiety on a substrate molecule, readily removed with appropriate reaction conditions known in the art. Preferably, the diallyloxyalkane is dimethoxypropane.

In another embodiment, the diol protection is achieved in the presence of a strong acid and a polar organic solvent. The strong acid may be selected from, without being limited thereto, p-TsOH, methane sulfonic acid, benzene sulfonic acid, formic acid, hydrochloric acid, sulfuric acid. The polar organic solvent may be, in accordance with another embodiment, a water-miscible solvent. A non-limiting example for the polar organic solvent is acetone. Others may include ethyl acetate, methylethyl ketone, chloroform, ethanol, methanol and others.

The term "functional group" is used herein to denote atoms or groups of atoms within molecules that are responsible for the physical and chemical characteristic of the molecule with respect to its physical properties and the possible reactions it may undergo with other reagents. A variety of functional groups are known with respect to chemical compounds. In accordance with one embodiment, the functional group is a diol group present on the furan ring. In an embodiment disclosed herein, the "diol" functional group refers to the two hydroxyl groups (—OH groups) attached to adjacent carbon atoms.

The term "oxidizing agent" as used herein refers to any substance in a reaction that gains electrons and whose oxidation number is decreased. In a typical reaction the oxidizing agent readily transfers oxygen atoms to a reactant, for example, the diol protected 6-halopurine of formula (III), thereby increasing its oxygen atoms content.

In the context of the present disclosure the terms "substitution" and "substituting", or "replacing" which may be used intechangibly, denote any replacement of an atom, a moiety, a functional group, or a substituent in a reactant molecule, by, independently, another atom, a moiety, a functional group, or a substituent in a reactant molecule.

In the context of the present disclosure the term "nucleophilic substitution" relates to a reaction in which an electron-rich reagent, having either a pair of unshared electrons or a negatively charged moiety, referred to as the "nucleophileic reagent" attacks a positive or partially positive moiety of a substrate molecule (for example the carboxylic carbon of an acyl chloride) and replaces a group or atom (also called a "leaving group", for example the chloride anion of the attached acyl chloride substrate).

In a further embodiment disclosed herein the oxidation of the primary alcohol in the diol protected 6-halopurine of formula (III) to the corresponding carboxylic acid derivative is executed in the presence of a catalytic amount of an oxidizing agent.

A non-limiting list of oxidizing agents which may be suitable for the oxidation of primary alcohols to the corresponding carboxylic acids, comprises ruthenium metal (Ru), ruthenium chloride, chromium trioxide, sodium periodate, potassium dichromate, potassium permanganate, silver oxide, nitric acid, platinum oxide/oxygen, 2,2,6,6-tetramethylpiperidine-1-oxyl (TEMPO), sodium chlorite and any combination thereof. Preferably, said oxidation is executed in the presence of a catalytic amount of $RuCl_3$ and sodium periodate.

The conversion of carboxylic acid derivative of formula (IV) to the respective methylamide derivative of formula (V) is executed by nucleophilic substitution in the presence of an halogenating agent and thereafter introducing the selected nucleophilic reagent, e.g. methylamine.

The term "halogenating agent" as referred to in the present context of the disclosure, concerns an agent capable of replacing a group or moiety in a molecule with a halogen atom. In the context of the present disclosure the halogenating agent replaces the hydroxyl group on the carboxylic acid moiety, thereby making it more prone to the nucleophilic substitution reaction with the methylamine nucleophile, since the group replaced would be a halogen anion, known to be a weak Lewis base, i.e. easily replaced by the nucleophile. Non-limiting examples of halogenating agents include thionyl chloride ($SOCl_2$), phosphorous pentachloride ($PCl_5$). Preferably, the halogenating agent is thionyl chloride.

Finally, the protecting group on the diol moiety of the furan ring is removed. Typically and without being bound by theory, the removal of protecting groups is a reductive cleavage reaction, preformed in the presence of strong acids. The removal of the diol protecting group may be performed in the presence of a strong acid and a polar non-protic solvent. In accordance with one embodiment, the strong acid is HCl and the solvent is tetrahydrofuran (THF). Other polar non-protic solvents known in the art may also be employed at this stage of reaction process, including but not limited to dimethyl sulfoxide (DMSO), dimethylformamide (DMF), dioxanes and hexamethylphosphorotriamide (HMPA).

In one embodiment, the method of producing IB-MECA is obtained in accordance with the following scheme:

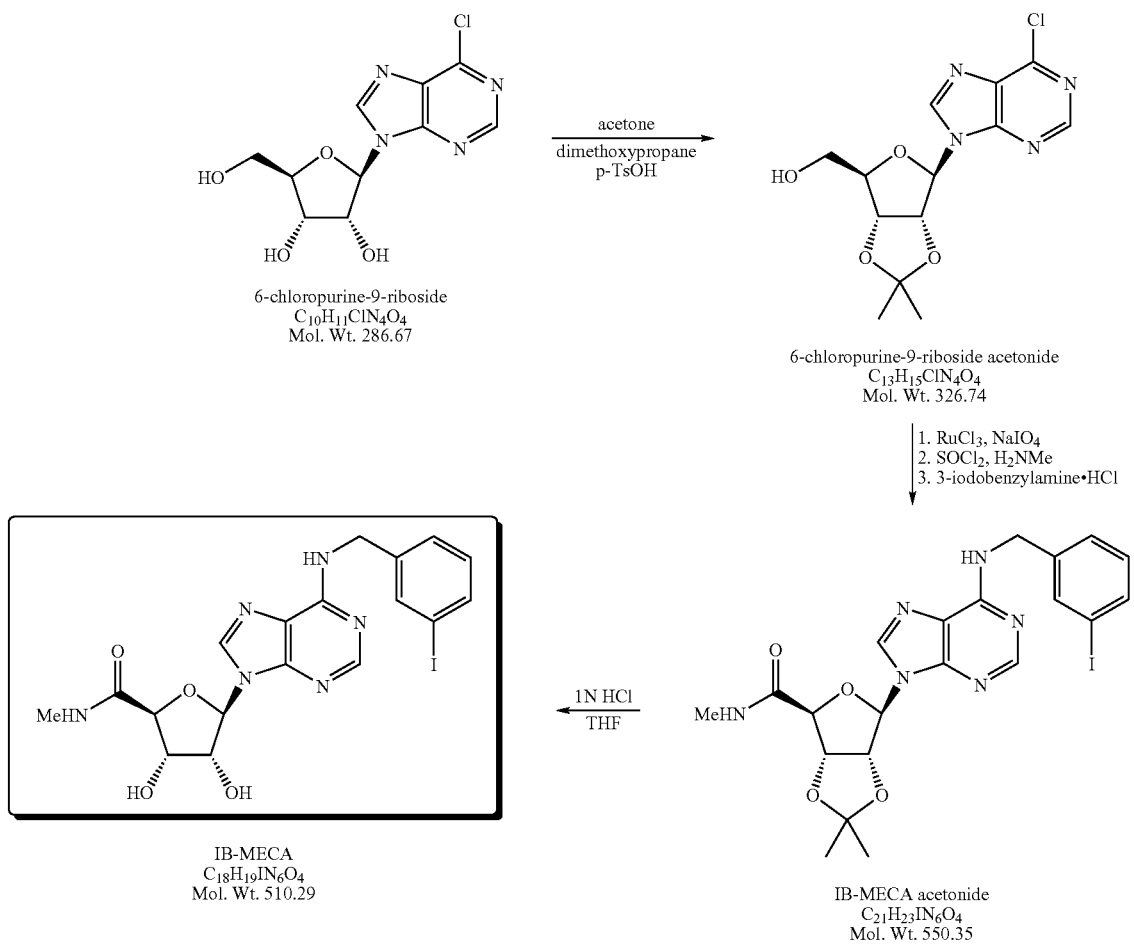

One advantage of the method of the invention is that it is applicable also large scale production of IB-MECA.

In the context of the present disclosure, large scale production refers to tens of grams to kilogram quantities of material of final product. As shown in the specific examples, there is no need for interim purification procedures. As appreciated by those versed in the art, interim purification steps lead to lower yields of the final product and therefore are typically not suitable for large scale productions. The method of the invention was found to be suitable for small scale as well as large scale production of IB-MECA.

Further, it was established that the method of the invention is suitable for Good Manufacturing Production (GMP) of IB-MECA. It is well known that GMP denotes the set of regulations, codes, and guidelines for the manufacture of drug substances (also known as active pharmaceutical ingredients (APIs)) and drug products (known as medicinal products in Europe), medical devices, in vivo and in vitro diagnostic products, and foods. In the United States, GMPs are referred to as "cGMP" or "*current Good Manufacturing Practices*". This term is recognized worldwide for the control and management of manufacturing and quality control testing of pharmaceutical products.

In another aspect of the present disclosure there is provided a chemically synthesized IB-MECA of formula (I), whenever obtained by any method of the invention.

In one further embodiment of the present disclosure there is provided a pharmaceutical composition comprising the chemically synthesized IB-MECA whenever obtained by the method of the invention.

The pharmaceutical composition of the invention may be used for the treatment or prevention of various diseases. The term "treatment" and the like are used herein to refer to obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment", as used herein, covers any treatment of a disease in a mammal, particularly a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; or (c) relieving the disease, i.e., causing regression of the disease and/or its symptoms or conditions.

A non-limiting list of diseases treatable by the composition of the invention comprise inflammation, as generally described in WO 2004/045627; WO 2005/063246; WO/2005/111053 and in WO 2006/059328; cancer, as generally described in WO2000/040251, and U.S. provisional patent application No. 60/838,863; dry eye as generally described in PCT patent application No. IL2006/000130; WO2006/011130 and in U.S. patent application Ser. No. 11/604,905; viral replication, as generally described in WO02/055085; osteoarthritis as generally described in PCT application No. IL2006/001374; as well as accelerated bone resorption as generally described in WO 2006/048884; the content of all the above applications being incorporated herein by reference.

EXAMPLES

Materials
6-Chloropurine-9-ribose (obtained from Wilshire Technologies)
p-TsOH $H_2O$ (obtained from Aldrich)
2,2-dimethoxypropane (obtained from Aldrich)
Ruthenium (III) chloride hydrate (obtained from Aldrich)
3-iodobenzylamine HCl (obtained from Apollo)
TBAI (obtained from Aldrich)
$CH_3CN$ (obtained from Fisher)
$H_2NCH_3$ (obtained from Aldrich)
$SOCl_2$ (obtained from Aldrich)
$NaIO_4$ (obtained from Aldrich)
Methods Example 1

Synthesis of IB-MECA

1. Preparation of Acetonide (III)
1.1 The Synthesis Procedure

6-Chloropurine-9-ribose acetonide (III) was prepared from commercially available 6-chloropurine-9-ribose (II) by treatment with 2,2-dimethoxypropane in the presence of catalytic p-toluenesulfonic acid.

The conversion of the riboside (II) to the acetonide (III) required approximately 48 hours to reach completion at 20-25° C. The workup method used is outlined below and involved quenching with aqueous sodium hydroxide, concentration of the mixture to dryness followed by an extractive aqueous workup into methylene chloride. Acetonide (III) was then isolated by drying over magnesium sulfate, filtration to remove the drying agent, solvent exchange into acetonitrile to precipitate the product, collection by filtration and drying in vacuo. A second crop of acetonide (III) was obtained by concentration of the mother liquors and isolation from slurry in acetonitrile. The combined (two crops) yield of acetonide (III) from 6-chloropurine-9-ribose (II) was 85.7%.

Following is an Outline of the synthetic step preformed for the preparation of acetonide (III) (all reagents, weight and volume equivalents are quoted with respect to the input of 6-chloro-9-riboside (II)):

Riboside of formula II (1 wt equiv) was added to acetone (23 vol) and agitation of the reaction mixture was initiated.

TsOH (0.05 equiv) and 2,2-dimethoxypropane (3.5 equiv) were then added to the reaction mixture.

The reaction mixture was stirred at 20° C.-25° C. for 48-96 hours during which samples were taken for determining reaction completion by HPLC. Completion condition was determined when riboside (II) is not more than (NMT) 2%.

The reaction was then quenched by the addition of 1N NaOH (0.052 equiv) and stirring for one hour.

The resulting mixture was then dried using rotary evaporation at 30° C.-40° C.

The resulting residue was then partitioned between $CH_2Cl_2$ (10 vol) and water (10 vol), stirred for 15 minutes and allowed to settle.

The phases were separated and the aqueous phase was extracted with $CH_2Cl_2$ (2×3 vol).

The organic extracts were combined and dried over $MgSO_4$ (2.5 wt equiv).

The mixture of extracts were filtered through a diatomaceous earth pad and the cake was with $CH_2Cl_2$ (1.5 vol).

The filtrate was concentrated to dryness by rotary evaporation at 30° C.-40° C.

The residue was slurred in $CH_3CN$ (2 vol) at 55° C.-65° C. for one hour.

The slurry was cooled to 0° C.-10° C., then aged at 0° C.-10° C. for at least one hour.

The product was then collected by filtration and washing the resulting cake with cold $CH_3CN$ (0.5 vol).

The product (the cake) was dried at 25°-35° C. to give acetonide of formula III (first crop). The expected yield was 59-76%; purity was 96.6 to 99.5%.

To increase yield, the mother liquor was recovered for second crop:

The filtrate was concentrated from the second crop to dryness.

The residue was slurred in $CH_3CN$ (0.15 vol) at 55° C. to 65° C. for at least 30 minutes.

The product was cooled to 0° C.-10° C. and aged at 0° C. for at least one hour.

The product (the cake) was collected by filtration and washed with cold $CH_3CN$ (0.03 vol).

The product was dried at 25° C.-35° C. to give acetonide of formula III (second crop). The expected yield was 9-14%; purity was 96.2 to 97.8%

Expected yield from two crops was 73-85%.

1.1 Optimization of the Process for Preparation of Acetonide (III)

Riboside of formula II (30 g) was reacted with 2,2-dimethoxypropane, using the established conditions (Steps 1-3, in above Outline), to give acetonide (III) as a solution in acetone. The mixture was quenched with 1N aqueous sodium hydroxide solution (Step 4, in above Outline) and split into portions.

1.2 Isolation of Acetonide (III) from Water

The acetone solution above was concentrated, by rotary evaporation under reduced pressure, to nine volumes then diluted with water (27 vol) and mechanically stirred for 20 minutes. The batch temperature increased from 23 to 28° C. and some precipitation was observed. The mixture was cooled to 4° C. and aged at 3-5° C. for one hour. Precipitation of the material as a fine crystalline solid was observed. The precipitate was collected by filtration, washed with water-acetone (2:1, 1.5 vol) and dried under vacuum (30 in. Hg) at ambient temperature to afford acetonide (III) as a pale yellow solid in 68% yield and 98.8% purity (AUC, HPLC).

In order to enhance the yield of acetonide (III), its isolation was preformed from a more concentrated acetone/water mixture. Therefore, the acetone solution was concentrated to nine volumes, as above, then diluted with water (9 vol) and stirred for 10 minutes The mixture was further concentrated to 12.5 volumes (the estimated acetone-water ratio was 2.6:1) and the product precipitated as a fine crystalline material. The mixture was cooled with stirring to 5° C., aged for 30 minutes then the product was collected by filtration, washed with water-acetone (2:1, 1.5 vol) and dried under vacuum at ambient temperature to afford acetonide (III) as a pale yellow solid in 80% yield and 99.3% purity (AUC, HPLC). Both the yield and purity of acetonide (III) were enhanced using this method.

1.3 Isolation of Acetonide (III) from Acetonitrile

The acetone solution was concentrated to six volumes, under reduced pressure, and the product precipitated from the quenched reaction mixture. Acetonitrile (15 vol) was required to solubilize the bulk of the solids. The mixture was clarified and the filtrate was concentrated by rotary evaporation under reduced pressure to three volumes. The resulting slurry was agitated at 60° C. (bath temperature) for one hour, then cooled to 5° C. and aged for one hour. The product was collected by filtration, washed with water-acetone (2:1, 1.5 vol) and dried under vacuum at ambient temperature to afford acetonide 2 as a pale yellow solid in 65% yield and 98.5% purity (AUC, HPLC).

It was clear from these experiments that acetonide (III) was relatively insoluble in both water and acetonitrile compared to acetone. The best results had been obtained by isolation of acetonide (III) from water/acetone. The reaction was repeated and acetonide (III) was prepared in 79% yield (27.1 g) and 99.54% purity (AUC, HPLC) from riboside (II) (30 g) using the modifications described above. The optimized conditions allowed the removal of the liquid-liquid extraction step, two evaporations to dryness and the need to isolate a second crop of acetonide (III). The improved efficiency of the workup procedure has significantly reduced the cycle time for the isolation of acetonide (III).

2. Process for the Preparation of Carboxylic Acid (IV)

2.1 The Synthesis Procedure

Acetonide (III) was converted to carboxylic acid (IV) by oxidation using a ruthenium trichloride/sodium periodate system in aqueous acetonitrile. The reaction is exothermic, warming relatively rapidly from 5° C. to 31° C. upon addition of the sodium periodate.

Following is an Outline of the synthetic steps for the preparation of carboxylic acid (IV):

1. Acetonide of formula III (1 wt equiv) and acetonitrile (14.9 vol) were placed in a reactor.
2. In addition, to the reactor $RuCl_3$ (0.01 wt, 1.6 mol %) was added and then water (4 vol).
3. Then, tertabutylammonium iodide (TBAI) was added to the reactor (0.01 wt, 1 mol %).
4. The resulting mixture was Cooled to <5° C.
5. To the cooled reaction mixture $NaIO_4$ (1.5 wt, 2 equiv) was added, in a portion-wise manner, maintaining the mixture's temperature at <30° C.
6. The mixture was stirred at 15° C.-30° C. and monitored by TLC for reaction completion.
7. The reaction product was filtered to remove inorganics and the filtered cake was rinsed with acetonitrile (6 vol).
8. The filtrate was concentrated on a rotovap to dryness at 30° C.-40° C. (bath temperature). At this stage the product decolorized by evaporation of volatile $RuO_4$.
9. The residue was slurred in THF (1.67 vol) at 15° C.-25° C. and transferred from the rotovap bulb into a clean reactor.
10. THF (18.5 vol) was added into the clean reactor and stirred for 30 minutes.
11. The product of step 10 was then filtered through a DE pad and the cake was rinsed with THF (0.66 vol).
12. The filtrate was concentrated to dryness by rotary evaporation at 30° C.-40° C.
13. The residue was slurred in $CH_3CN$ (2.33 vol) at 30-40° C. until fully mobile.
14. The product of step 13 was then concentrated to dryness by rotary evaporation at 30° C.-40° C.
15. IPAc (Isopropyl acetate) (17.5 vol) was added in portions to a reactor via the rotovap bulb, and the reaction product was transfered to the reactor.
16. Water (5 vol) was also added to the reactor and the mixture in the reactor was stirred for two hours.
17. The phases were separated and the organic phase was washed with water (5 vol).
18. The aqueous phases were combined and back-extracted with IPAc (3 vol).
19. The organic phases were combined and dried over $Na_2SO_4$ (1.67 wt equiv) for one hour.
20. The product was filtered to remove the drying agent and the filtrate (cake) was rinsed with IPAc (2 vol).
21. The filtrate was then collected to dryness by rotary evaporation (30° C.-40° C.).
22. The residue was then dried in a vacuum oven at 30° C.-40° C. to constant weight. The solid was ground and drying continued until constant weight was achieved. Expected yield was 85%, expected purity was 92-93% (HPLC).

2.1 Optimization of the Workup for Carboxylic Acid (IV)

A. sample was removed from the batch and cooled to 6° C. and very thick slurry was formed. Acetonitrile (4 vol) was added, which dissolved the majority of the solid material, and the mixture was again concentrated to four volumes. Upon cooling to 6° C., and holding for one hour, the sample formed well behaved slurry. The product was collected by filtration, washed with water and dried to give acid 3 as an off-white solid in 95.3% purity (AUC, HPLC).

The remainder of the reaction mixture was worked up as described in the above procedure to give carboxylic acid (IV) in 77% yield containing 7.0 wt % IPAc. This compares with the previous cGMP, result for preparation of acetonide (III) of 85% yield containing 7.4 wt % (IPAc).

The oxidation reaction was repeated and carboxylic acid (IV) was isolated by crystallization from water/acetonitrile as described for the sample above. On this occasion, the reaction mixture did not decolorize during the initial acetonitrile/water strip (Step 8 in the above Outline) and carboxylic acid (IV) was isolated as a gray solid in 78% yield and 97.9% purity (AUC, HPLC). Such "non-decolorization" behavior, tentatively ascribed to running the oxidation reaction at <25° C., was observed during preparation of a previous cGMP batch of IB-MECA and did not impact the quality of the API produced. Karl Fischer analysis indicated the batch contained 0.19% water.

2.2 Control of Delayed Exotherm in the Preparation of Carboxylic Acid (IV)

The oxidation of acetonide (III) was accompanied by a delayed exotherm, following addition of sodium periodate. Interruption of active cooling results in rapid warming of the batch from 5 to 30° C. This presents a significant safety hazard, particularly upon thither scale-up to fixed manufacturing equipment.

In order to better control the exotherm an inverse addition of the substrate (acetonide (III)) to the mixture of ruthenium trichloride and sodium periodate was preformed. Acetonide (III) (5 g) was added as a solution in acetonitrile-water to the oxidant mixture in water at 30-35° C. over two hours. The reaction was complete after 16 hours as regularly observed for the usual mode of addition. Using the improved workup conditions but cooling to 20° C. instead of 5° C., acid 3 as a white solid in 62% yield and 99.3% purity (AUC, HPLC). A second crop of material was isolated by filtration of the mother liquors, where further crystallization had occurred, washing with water and drying afforded acid 3 as an off-white solid in 19% yield and 98.2% purity (AUC, HPLC). The combined yield for two crops of acid 3 was 81%. Both crops were suitable for use in the next step (i.e., preparation of IB-MECA acetonide (VI)).

2.3 Optimizing the Conditions for Carboxylic Acid (IV)

Acetonide (III) (25 g) was converted to carboxylic acid (IV) employing the inverse addition of the substrate to the oxidizing mixture. When the oxidation was complete, the batch was filtered to remove inorganic impurities and the filter cake was washed with acetonitrile (6 vol). The filtrate was diluted with additional water (3 vol) to give a solution of carboxylic acid (IV) in acetonitrile (approximately 21 vol) and water (approximately 7 vol) The batch was concentrated by vacuum distillation at 26-36° C. to eight volumes. The estimated acetonitrile-water ratio at this point was 40:60 respectively. The batch was cooled to 5-10° C. to induce crystallization and aged for one hour. The product was collected by filtration, washed with water and dried to give acid 3 as a white solid in 75% yield and 99.75% purity (AUC, HPLC).

This optimized process eliminated the need for an extractive workup, use of THF and IPAc, one filtration and four evaporations to dryness. The cycle time for isolation of carboxylic acid (IV) was significantly reduced and the product was isolated in an easily handled form. When corrected for IPAc content, the yields for the existing and newly developed procedures were comparable (77 versus 75% respectively) and carboxylic acid (IV) was isolated in higher purity by crystallization from acetonitrile-water (97.9-99.7%).

3. Process for the Preparation of IB-MECA Acetonide (VI)

Carboxylic acid (IV) is converted to IB-MECA Acetonide (VI) over three steps as outlined below. Carboxylic acid (IV) was first converted to acid chloride by treatment with thionyl chloride in acetonitrile, then to amide (V) by reaction with methylamine in the presence of diisopropylethylamine (DIPEA). Coupling of amide (V) with 3-iodobenzylamine hydrochloride gives IB-MECA Acetonide (VI). Intermediates acid chloride and amide (V) are not isolated.

3.1 Purification of 3-iodobenzylamine Hydrochloride

The quality of 3-iodobenzylamine hydrochloride had significant impact on the outcome of the synthesis. In particular, 3 hydrochloride, an impurity present in 3-iodobenzylamine hydrochloride, and impurities derived thence, were known to persist during downstream processing including the API. An upper limit of ≤0.5% was established for 3 bromobenzylamine hydrochloride in 3-iodobenzylamine hydrochloride for the successful preparation of IB-MECA. Since a suitable commercial supply of 3-iodobenzylamine hydrochloride was not available for the optimization work, methods for purification were investigated.

A solubility study was performed on 3-iodobenzylamine hydrochloride using the solvents employed in the synthesis of IB-MECA the results of which are outlined in Table 1 below. 3-Iodobenzylamine hydrochloride recrystallized from protic solvents but was insoluble in aprotic organic solvents. No purity enhancement was observed during hot (reflux) slurries in aprotic organic solvents.

TABLE 1

Solubility Study on 3-iodobenzylamine hydrochloride

| | Solvent | Solvent Volumes | Behavior at 21 C. | Behavior at reflux | Comments |
|---|---|---|---|---|---|
| 1 | MeOH | 1 | Insoluble | Soluble | Recrystallized, no purity enhancement |
| 2 | MeCN | 5 | Insoluble | Insoluble | Hot slurry did not enhance purity |
| 3 | IPAc | 10 | Insoluble | Insoluble | Hot slurry did not enhance purity |
| 4 | IPA | 10 | Insoluble | Soluble | Recrystallized, no purity enhancement |
| 5 | THF | 10 | Insoluble | Insoluble | Hot slurry did not enhance purity |

Recrystallization from water (4 vol) reduce the level of 3-bromobenzylamine hydrochloride in 3-iodobenzylamine hydrochloride to within acceptable levels. In order to generate a supply for use in the proof-of-concept run 3-iodobenzylamine hydrochloride (150 g, ex. Apin) was recrystallized from water in 78.6% yield. The concentration of 3-bromobenzylamine hydrochloride was reduced from 0.92% to 0.38%.

A batch of carboxylic acid (IV), prepared using the modified conditions, was converted to IB-MECA acetonide (VI) using the procedure outlined below. All reagent, weight and volume equivalents are quoted with respect to the input of carboxylic acid (IV).

1. The carboxylic acid derivative of formula IV (1 wt equiv) was mixed with acetonitrile (10 vol) which formed a heavy slurry and the heavy slurry was agitated at 20° C.-25° C.;
2. To the agitated slurry a halogenating agent, namely, thionyl chloride (1.6 equiv) was added and the mixture was stirred for at least one hour to form a solution;
3. The reaction was monitored for completion by TLC eluting with IPAc-MeOH (10:1).
4. The reaction solution was concentrated to an oil (to remove the thionyl chloride) by rotary evaporation at 20° C. (bath temperature).
   Acetonitrile (0.5 vol) was added and the mixture was concentrated to oil once more. This oil comprised concentrated acid chloride.
5. The acid chloride was re-dissolved in acetonitrile (10.4 vol) and cooled to <2° C. while stirring.
6. Methylamine (2M solution in THF, 1.05 equiv) was added and the mixture temperature was maintained at <5° C. A white precipitate (suspected methylamine hydrochloride) was observed in the reactor.
7. the product was stirred at <5° C. for at least 15 minutes.
8. DIPEA (1.5 equiv) was then added and the temperature of the system was maintained at <5° C.
9. Active cooling was discontinued and the reaction mixture was allowed to warm to 20° C. over approximately two hours.
10. The reaction was monitored for completion by TLC eluting with IPAc-MeOH (10:1). When complete, a solution of amide (V) in MeCN/THF was obtained.
11. To the solution of amide (V) 3-iodobenzylamine hydrochloride (1.35 equiv) was added followed by DIPEA (5.0 equiv).
12. The mixture was heated to 70° C. and monitored for reaction completion by HPLC. The expected reaction time was 14-16 hours and the completion condition was ≤0.7% amide (V) remaining.
13. When completed, the product was cooled to <40° C. and concentrated to an oil by rotary evaporation. foaming at this point was especially avoided.
14. The residue was then dissolved in IPAc (8 vol).
15. to the dissolved residue saturated aqueous NaHCO$_3$ (7 vol) was added and the mixture was agitated for at least 30 minutes.
16. Stirring was then stopped to allow settling, and separation of the phases.
17. The organic phase was washed with water (4 vol).
18. The combined aqueous phases were back extracted with IPAc (2×3.4 vol).
19. The organic extracts were combined and concentrated to a residue by rotary evaporation.
20. The product was then slurried in MeOH (4 vol) then concentrated to a residue by rotary evaporation.
21. MeOH (4 vol) was then added to the product of step 20 and heated to dissolution (approximately 65° C.) with stirring.
22. the product of step 21 was then cooled to <30° C. to induce crystallization.
23. The crystallized product was then collected by filtration and the filter cake was washed with chilled (13° C.) MeOH (1.8 vol).
24. The cake was dried at 30° C.-40° C. in vacuo to give IB-MECA acetonide (VI).
25. The recrystallization from MeOH and drying was repeated as necessary to obtain IB-MECA acetonide (VI) within release specifications. Expected yield was 48%.

IB-MECA acetonide (VI) was isolated as a white solid in 80% yield and 99.52% purity (AUC, HPLC) after a single recrystallization from methanol. The impurity derived from 3-bromobenzylaine hydrochloride was observed at a concentration of 0.21% (specification: ≤0.5%) and all other impurities were <0.1%. These results demonstrated that the modifications used to prepare acetonide (III) and carboxylic acid (IV) produced material which was suitable for use in the preparation of IB-MECA acetonide (VI). They also implied that use of higher quality acid 3 (98.2-99.3% purity, previously 92-93%) allowed preparation of IB-MECA acetonide (VI) in very high purity without the need for multiple recrystallizations. HPLC data also indicated that amide (V) can be successfully purged from an IPC concentration of up to 2.3% during isolation of IB-MECA acetonide (VI).

4. Process for the Preparation of IB-MECA (I)

IB-MECA (I) was prepared by deprotection of IB-MECA acetonide (VI) using aqueous hydrochloric acid.

The batch of IB-MECA acetonide (VI) above was deprotected, using the method steps outlined below (Steps 1-10), to give IB-MCA (I) as a white solid in 90% yield and 9.67% purity (AUC, HPLC). The concentration of the impurity derived from 3-bromobenzylamine hydrochloride was 0.18% and no other impurities were >0.1%.

1. IB-MECA acetonide (VI) (1 wt equiv) and THF (5 vol) were added to a reactor.
2. Agitation was initiated followed by the addition of 1N hydrochloric acid (5 vol). The mixture warmed from 16° C. to 25° C.
3. Then, the mixture was actively heated to 50° C. and reaction completion was monitored by HPLC. Completion condition: ≤1.5% acetonide remaining. The expected reaction time was eight hours. If not complete after eight hours, the batch temperature was lowered to 40° C. to avoid formation of impurities.
4. The product was filtrated at 40° C.
5. The filtered product was then cooled to at least 15° C. then quenched into saturated NaHCO$_3$ (15 vol) maintaining temperature at 10° C.-25° C. The product precipitated on contact with the base.
6. The mixture was stirred at 10° C.-25° C. for at least 12 hours.
7. The solids were collected by filtration and the filtered cake was rinsed with H$_2$O (5×0.95 vol).
8. The washed product was then slurried in methanol-water (9:1, 9.9 vol) at 50° C. for at least 30 minutes then cooled to 15° C.-25° C.
9. The product was collected by filtration and the filter cake was washed with methanol-water (9:1, 0.27 vol).
10. The product was dried at 30° C.-40° C. in vacuo to give IB-MECA (I), expected yield was 81%.
11. The product was re-slurred in water (4.14 vol) at 35° C.-45° C. for at least three hours.
12. The re-slurred product was then cooled to 25° C. then collected by filtration.
13. The filtered cake was washed with water (2×1 vol).
14. The washed cake was then dried at 55° C.-65° C. to give IB-MECA (I). Expected recovery was 78%.

Example 2

Proof-of-Concept for Large Scale Synthesis of IB-MECA (I)

In order to demonstrate the optimized conditions developed for the synthesis of IB-MECA (I) from 6-chloropurine-9-riboside (II), the procedures above were preformed for the preparation of 50 g of IB-MECA (I). Thus, 6-chloropurine-9-riboside (II) was converted to acetonide (III) using the method described below. All reagent, weight and volume equivalents are quoted with respect to the input of riboside Optimized Method for Preparation of Acetonide (III)
1. Riboside (II) (1 wt equiv) was added to a reactor followed by the addition of acetone (23 vol) and agitation.
2. To the reactor TsOH (0.05 equiv) was then added followed by 2,2-dimethoxypropane (3.5 equiv).
3. The mixture was stirred at 20° C.-25° C. for 48-96 hours and tested for reaction completion by HPLC. Completion condition: riboside NMT 2%.
4. The reaction was quenched by addition of 1 N NaOH (0.052 equiv) and stirring for one hour.
5. The product was concentrated by rotary evaporation (30° C.-40° C.) to nine volumes.
6. Water (9 vol) was then added.
7. The product was then concentrated by rotary evaporation (30° C.-40° C.) to 12.5 volumes.
8. The mixture was cooled to 0° C.-5° C.; and maintained at 0° C.-5° C. for at least one hour.
9. Collect the product by suction filtration, followed by rinsing with cold (0° C.-5° C.) $H_2O$/acetone (2:1, 1.5 vol).
10. The product was then dried at 40° C. to give acetonide (III). Expected yield was 79%.

Acetonide (III) was isolated as a white solid as pale yellow crystals in 82.2% yield (153.1 g) from 6-chloropurine-9-riboside (II) (163.3 g) in 99.58% purity (AUC, HPLC). The reaction was complete after 63 hours (Step 3 in Outline above) and was held overnight (14 hours) at the end of Step 7. The temperature of the batch immediately prior to filtration in Step 9 (in Outline above) was 2° C. and the drying time was 17 hours. No processing issues were encountered in the running of the batch. Acetonide (III) (147.2 g) was carried forward and converted to acid 3 using the method described below. All reagent, weight and volume equivalents are quoted with respect to the input of acetonide (III).

Optimized Method for Preparation of Carboxylic Acid (IV)
1. $NaIO_4$ (2.30 equiv), TBAI (1 mol %) and water (2 vol) was added to a reactor and stirred to form a slurry.
2. $RuCl_3$ (1.6 mol %) was added and the weighing vessel was rinsed with water (1 vol).
3. The reactor mixture was heated to 30° C. with stirring.
4. Acetonide (III), as a solution in acetonitrile (12 vol) and water (1 vol) were charged to the reaction mixture and the temperature was maintained at 30° C.-35° C. The addition was expected to take two hours to complete. When the addition is complete, the vessel which contained the acetonide (III) solution with acetonitrile (3 vol) was rinsed and add to the product.
5. The mixture was cooled at 30° C.-35° C. and monitored for reaction completion by TLC. The expected reaction time is 16 hours.
6. the product was cooled at 20° C.-25° C. and filtered to remove inorganic impurities.
7. The reactor and filter cake were rinsed with acetonitrile (6 vol) and the filtrates were diluted with water (3 vol).
8. The filtrates were concentrated to eight volumes by rotary evaporation at 25° C.-35° C. At this stage the produce decolorized by evaporation of volatile $RuO_4$.
9. The product was cooled to 5° C.-10° C. to induce crystallization and aged for at least one hour.
10. The product was then collected by filtration and the filter cake was washed with water (3×3 vol).
11. The product was dried at 35° C.-45° C. in vacuo to give acid (IV). Expected yield is 75%.

Acetonide (III) was charged to the reaction mixture over three hours and reached a maximum batch temperature of 36° C. The oxidation was complete after 14 hours (TLC analysis). Upon cooling to 20° C.-25° C. (Step 6 in Outline above) the batch unexpected darkened, changing from orange to green, indicating a change in the oxidation state of the ruthenium species from $Ru^{VI}$ to $Ru^{II}$. Also, the batch did not decolorize during the concentration to reduce the concentration of acetonitrile. Acid (IV) was ultimately isolated as a dark green solid in 63% yield (96.2 g) and 98.9% purity (AUC, HPLC). Since previous studies had shown that the color causing impurities were purged during downstream processing the product was carried forward without further purification. Carboxylic acid (IV) (75 g) was converted to IB-MECA acetonide (VI) using the method described in Example 1.

The chlorination reaction, to prepare acid chloride, was complete after 70 minutes (Step 3 in Outline in Example 1) and the batch foamed considerably during concentration (Steps 4 and 5 in Example 1). Methylamine (2M solution in THF) was added to the acid chloride solution over 16 minutes and the maximum batch temperature was 5° C. Conversion of acid chloride to amide (V) was complete after two hours during which time the batch warmed from 5° C. to 17° C. (Steps 10 and 11 in Example 1). Coupling of 3-iodobenzylamine hydrochloride with amide (V) required 16 hours to reach completion (Step 13 in Example 1). During the extractive workup, a significant quantity of solid material was observed. At Step 17 (in Example 1) excess $NaHCO_4$ precipitated from the mixture and can be overcome by the addition of more water During Step 18 (in Example 1) the product precipitated and required the addition of water (5 vol) and IPAc (5 vol) to redissolve IB-MECA acetonide (VI). HPLC analysis of the aqueous layer at the end of Step 18 (in Example 1) indicated that IB-MECA acetonide (VI) was not present in a significant concentration. As such, the back-extractions of the aqueous phase with IPAc (Step 19 in Example 1) were omitted. IB-MECA acetonide (VI) was ultimately isolated as a pale green solid in 75.2% yield (91.6 g) and 99.79% purity. The "bromo-impurity", present in 3-iodobenzylamine hydrochloride at 0.38%, was observed at a relative concentration of 0.21%. The batch was significantly but not completely decolorized (input carboxylic acid (IV) was dark green) at the end of the isolation procedure.

IB-MECA acetonide (VI) (85 g) was deprotected, using the method outlined in Example 1, to give IB-MECA (I) as a white solid in 84.5% yield (67 g) and 99.83% purity. The acetonide cleavage was complete after 9.5 hours (Step 3 in Example 1) and the product decolorized during collection after the methanol-water slurry (Step 9 in Example 1). After the slurry in water to remove residual methanol, the product filtered very slowly and was transferred to the dryer with great difficulty. The purity of IB-MECA was unchanged between its initial isolation from methanol-water and after re-slurry from water.

Example 3 cGMP Production of IB-MECA (I)

cGMP Manufacture of 6-Chloropurine-9-riboside Acetonide

To a 200-L reactor with moderate stirring were charged acetone (115 L, 23 vol) and 6-chloropurine-9-riboside (5.0 kg, 17.4 mol, 1.0 wt/1.0 vol). Subsequently, p-TsOH·H$_2$O (166 g, 0.88 mol, 0.05 equiv, 0.033 wt) and 2,2-dimethoxypropane (7.6 L, 62 mol, 3.54 equiv, 1.52 vol) were added and the resulting yellow suspension stirred at ambient temperature. After 45 h, a sample of the resulting yellow-green solution was taken and analysis by HPLC revealed the starting material to be present at 0.42% by conversion (overall purity 96.9 area %). The batch was neutralized by the addition of 1N NaOH (900 mL, 0.90 mol, 0.05 equiv, 0.18 vol). This addition took approximately 2 min; the final pH was pH 7. The batch was allowed to stir for 1 h. The resulting cloudy yellow mixture was concentrated under reduced pressure at 35±5° C. on the rotary evaporator over a period of 8 h, until a volume of 45 L (9.0 vol) was achieved. The concentrate was stored under N$_2$ at 2-8° C.

The concentrate was transferred to a 200-L reactor and stirring commenced. Water (45 L, 9.0 vol) was added and the resulting dilute suspension was stirred for 55 min. The batch was transferred portionwise to a 72-L reactor assembled in a heating mantle equipped for vacuum distillation. Distillation at 35±5° C. commenced and proceeded until a batch volume of 62 L (12.4 vol) was achieved (The distillation was conducted over a period of two days, and included 15 hours of aging at ≤30° C. once complete). The batch was transferred to a 72-L reactor assembled in a cooling bath. The batch was chilled over a period of 4½ h until the temperature reached ≤5° C. and was stirred for an additional 1 h. The solids were filtered employing Sharkskin filter paper and the cake was rinsed with chilled 2:1 water/acetone (7.5 L, 1.5 vol) (The total filtration time was approximately 1 hour 40 minutes and included pulling N$_2$ through the cake in order to help it dry). The damp solids (5.99 kg) were transferred into six glass drying trays and dried under vacuum in an oven at 40±5° C. After drying for 47 h, the batch was packaged in 4-mil LDPE (double bags) under N$_2$ and stored in a fiber drum. This afforded 6-chloropurine-9-riboside acetonide (4505 g, 79%).

cGMP Manufacture of IB-MECA Acetonide

To a 72-L reactor supported in a cooling bath, was charged CH$_3$CN (37 L, 14.8 vol). Stirring commenced at ambient temperature. To this was added 6-chloropurine acetonide (2234 g and 266 g, total=2500 g=1.0 wt=1.0 vol, 7.65 mol), ruthenium(III) chloride hydrate (25 g, 0.121 mol, 0.016 equiv, 0.010 wt), water (10 L, 4.0 vol), and TBAI (25 g, 0.068 mol, 0.009 equiv, 0.010 wt). The resulting mixture was cooled to 5° C. over 1 h employing an ice-water cooling bath, and NaIO$_4$ (3750 g, 17.5 mol, 2.3 equiv, 1.5 wt) was added over 2 min while maintaining the internal batch temperature <10° C. The ice/solvent bath was emptied after 50 min and the batch was allowed to warm to ambient temperature (The batch temperature reached a maximum of 33° C. over a period of two hours. A cold-water bath was applied to prevent the batch temperature from exceeding this temperature). The resulting thick brown-orange suspension was stirred at 15-30° C. for 21 h. Analysis by TLC (IPAc, UV detection) showed the disappearance of the 6-chloropurine-9-riboside acetonide. The yellow suspension (21° C.) was filtered over a period of 30 min until dripping ceased; CH$_3$CN (15 L, 6.0 vol) was employed as a rinse of the reactor and cake. The filtrate was concentrated in three portions on the rotary evaporator with the water bath set at 40±5° C. over a period of 11 h.

To a 72-L reactor were charged the resultant residue (7.7 kg) and purified water (22.5 L, 9 vol). Stirring at ambient temperature was commenced. After 1 h, the batch (23° C.) was filtered, and the reactor and the cake were rinsed with purified water (7.5 L, 3 vol). The damp cake (4.7 kg) was transferred to six drying trays and dried in the vacuum oven set at 40° C. for six days. The IPC KF (specification set at <0.6%) and $^1$H NMR (DMSO-d$_6$) showed acceptable material. This afforded 6-chloropurine acid (2145 g, 82%) which was stored under N$_2$ in amber glass jars with Teflon lined lids.

Typical Procedure for the Manufacture of Crude IB-MECA Acetonide

To a 72-L reactor, was charged 6-chloropurine acid [2600 g, 7.63 mol, 1.0 wt=1.0 vol] using CH$_3$CN. (31.7 L, 12.2 vol) to effect the transfer, and stirring commenced. Thionyl chloride (889 mL, 12.2 mol, 1.60 equiv, 0.342 vol) was added to the thick gray slurry and the mixture stirred at <30° C. for 4 h. Approximately 0.5 mL of the resultant dark solution was added to MeOH (2 mL, HPLC grade, Fisher), and analysis by TLC (UV detection, IPAc/MeOH, 10:1) showed the disappearance of the starting material. Over a period of 6.5 h, the batch solution was concentrated under vacuum on the rotary evaporator until distillation ceased (the water bath was initially set at 25±5° C. and gradually increased to 35±5° C. for this); CH$_3$CN (825 mL, 0.32 vol) was used to rinse the reactor. The water-bath heat source was switched off and CH$_3$CN (7.6 L, 2.9 vol) added to the residue in the bulb. Without vacuum, the bulb was rotated until the batch became fully mobile and then it was transferred to a 72-L reactor positioned in a steel tub. Stirring was commenced and additional CH$_3$CN (25.5 L, 9.8 vol) was added. The batch was cooled using an ice-water/solvent bath until the internal batch temperature was <2° C. (this took 1 h); then 2 M methylamine in THF (4004 mL, 8.01 mol, 1.05 equiv, 1.54 vol) was added via a 5-L addition funnel over a period of 52 min while maintaining the internal batch temperature <7° C. Subsequently, DIPEA (1976 mL, 11.3 mol, 1.5 equiv, 0.76 vol) was added via a 5-L addition funnel over 1 h; stirring was continued at <7° C. for a minimum of 1 h, the cooling bath was drained, and stirring continued for 11 h while the batch was allowed to warm to ambient temperature (the pH of the batch was 9). Typically the minimum temperature of the batch for these operations was 0° C. Analysis by TLC (UV detection, IPAc/MeOH, 10:1) showed the disappearance of the 6-chloropurine acid/acyl chloride and the formation of one higher-running major product. The batch was transferred to another 72-L reactor setup in a heating mantle, equipped with a water-cooled condenser; CH$_3$CN (1.3 L, 0.5 vol) was used to aid with the transfer. Stirring was commenced and 3-iodobenzylamine.HCl (2777 g, 10.30 mol, 1.35 equiv, 1.068 wt) was added. Subsequently, DIPEA (6656 mL, 38 mol, 5.0 equiv, 2.56 vol) was added and the mixture heated at 70±5° C. for 25 h. Analysis by HPLC showed 0.70% of the 6-chloropurine amide remaining by conversion, thus just meeting the ≤0.70% specification. The heat source was switched off and the batch allowed to cool overnight. Over a period of 8 h, the batch was concentrated under vacuum on the rotary evaporator at 40±5° C. until distillation ceased; CH$_3$CN (1650 mL, 0.63 vol) was used to rinse the reactor. With the aid of IPAc (5.36 L, 2.1 vol), the residue was transferred to a 72-L reactor. Additional IPAc (20.4 L, 7.85 vol) was added to the reactor and stirring initiated. To this was added saturated aqueous sodium bicarbonate (22.2 L, 8.5 vol). After 30 min of stirring, the biphasic system was allowed to settle for 10 min and the lower aqueous phase collected (additional water (5 L) was added to dissolve the minor amount of remaining solids in the biphasic mixture). The remaining organic phase was washed with water (12.7 L, 4.9 vol) with 25-min stirring time and 38-min settling time. The combined organic phase was concentrated under vacuum on the rotary evaporator at 40±5° C. until distillation ceased (over a period of 6 h). The carboy was rinsed with IPAc (825 mL, 0.32 vol). In stages the resulting residue was slurried in the rotary evaporator bulb with MeOH (12.7 L, 4.9 vol) and concentrated until distillation ceased (4.5 h). This afforded crude IB-MECA acetonide (7.2 kg) as a damp beige solid which was stored for further processing and batch combination. Analysis by HPLC showed IB-MECA acetonide at 91.3 area % purity.

Purification of Crude IB-MECA Acetonide

The crude MeOH damp IB-MECA acetonide (15 kg, 91 area %) was recrystallized from MeOH (34 L) at 60-65° C. The resulting filter cake was rinsed with chilled MeOH (15.3 L) and transferred to eight drying trays (batch weight 10 kg) Analysis by HPLC showed IB-MECA acetonide at 65 area % purity present in the filtrate. It was estimated from the peak height that 1 kg of this material was sacrificed to this operation. The batch was dried in the vacuum oven set at 40° C. for approximately 22 h (7945 g). Analysis by HPLC showed the desired product at 99.0 area % purity contaminated with two significant impurities at RRT 0.64 (0.32 area %) and RRT 1.30 (0.58 area %). The mass spectra of these peaks are:
  RRT=0.64
  MW=424.19
  m/e: 424.19 (100%), 425.19 (23.9%), 426.19 (4.0%), 425.18 (2.2%)
  C, 59.42; H, 5.70; N, 19.80; O, 15.08.
  RRT 1.30
  MW=752.34 gr/mol
  m/e: 752.01 (100.0%), 753.01 (32.4%), 754.02 (4.5%), 754.01 (1.5%)
  C, 43.10; H, 3.48; I, 33.74; N, 11.17; O 8.51

This material was recrystallized again from MeOH (23.8 L) at 60-65° C. The resulting filter cake was rinsed with chilled MeOH (2×8 L). The total filtration time was 85 minutes. The cake was stored under a flow of $N_2$. Analysis of the cake by HPLC showed the desired product at 99.77 area % purity contaminated with two significant minor impurities at RRT 0.64 (0.07 area %) and RRT 1.30 (0.16 area %). The batch was transferred to six drying trays (batch weight 7.4 kg) rather than perform the third optional recrystallization. The batch was dried in the vacuum oven set at 40° C. for approximately 60 h. This afforded IB-MECA acetonide (7097 g) as a white solid after packaging into four amber glass jars; storage was at ambient temperature.

cGMP Manufacture of IB-MECA

To a 72-L reactor were charged THF (18.1 L, 5.1 vol), IB-MECA acetonide (3.55 kg, 6.45 mol, 1.0 wt/1.0 vol), and 1N aqueous HCl (17.8 L, 17.8 mol, 2.76 equiv, 5.0 vol). The resulting pale green stirring slurry was heated at 50±5° C. for approximately 8 h at which point HPLC analysis showed 1.16% of IB-MECA acetonide remaining wrt IB-MECA (thus meeting the specification ≤1.5%). The batch was allowed to cool to approximately 40° C. and then filtered through an in-line filter via a transfer pump. The emptied reactor and the transfer line were rinsed with THF (600 mL, 0.17 vol). The resulting filtrate was stored in the cold room (2-8° C.) overnight. To a 200-L reactor was added chilled saturated aqueous $NaHCO_3$ (53.6 L, 15 vol, 16° C.) through an in-line filter and stirring commenced. The IB-MECA rich filtrate (15° C.) was added over 30 min to the 200-L reactor via a transfer pump equipped with an in-line filter. The resulting white precipitate was stirred overnight to age (there was little temperature fluctuation during the precipitation which occurred at 20±2° C., no cooling was applied, and there was a minor amount of foaming. The pH of the slurry was pH 7.5). The batch was filtered using a nylon filter cloth; the emptied reactor and the cake were rinsed with water (5×3.4 L, 4.8 vol). The cake was pulled under a flow of N2 (total filtration time was 5.5 h), packaged for further processing, and stored in the cold room. This batch (92 kg wet weight) was shown to be 99.5 area % pure with no single impurity >0.20 area % by HPLC.

Example 4

Comparative Kilo-Scale cGMP Production Processes of IB-MECA

Scheme 1 represents the procedures employed for a kilo-scale preparation of IB-MECA in accordance with the present disclosure and as defined in the appended claims (typical yields and HPLC purities are shown). The production steps represented in Scheme 1 are similar to the production processes for the preparation of IB-MECA detailed in Example 1 above. A single batch production of IB-MECA using this process was as, much as 6 kg (99.5 area % pure by HPLC, with no single impurity >0.18%). The cGMP production started with the commercially available 6-chloropurine-9-ribososide (10 kg) and afforded IB-MECA (6 kg, 34% overall theoretical yield (60 wt %)).

Scheme 2 represents a variation in the production process of IB-MECA (typical yields and HPLC purities are also shown). The difference resides in the work-ups, order of reactions, equivalents of reagents charged, solvents employed, and subsequent yields. The procedures in Scheme 2 employed both silica gel column chromatograph and reverse phase Biotage purification. The process of Scheme 2 was performed on 350-g and 2-kg scales and afforded IB-MECA (32 g, 9 wt %) and (414 g, 21 wt %), respectively.

Scheme 1. Process for the production of IB-MECA (CF101)

Step A:

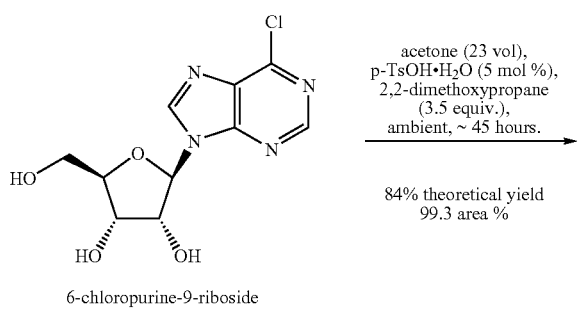

6-chloropurine-9-riboside acetone (23 vol), p-TsOH•H2O (5 mol %), 2,2-dimethoxypropane (3.5 equiv.), ambient, ~ 45 hours.

84% theoretical yield
99.3 area %

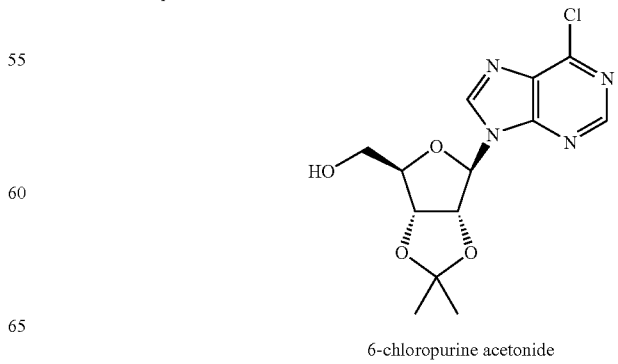

6-chloropurine acetonide

-continued

Step B:

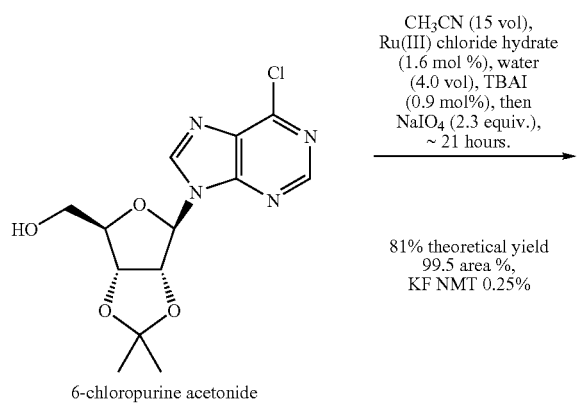

6-chloropurine acetonide

CH₃CN (15 vol),
Ru(III) chloride hydrate
(1.6 mol %), water
(4.0 vol), TBAI
(0.9 mol%), then
NaIO₄ (2.3 equiv.),
~ 21 hours.

81% theoretical yield
99.5 area %,
KF NMT 0.25%

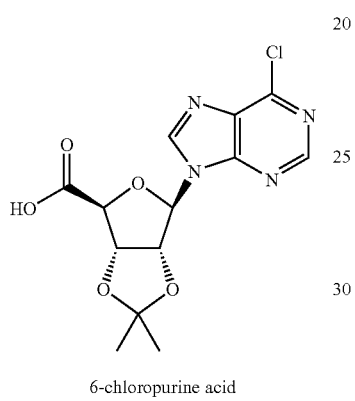

6-chloropurine acid

Step C:

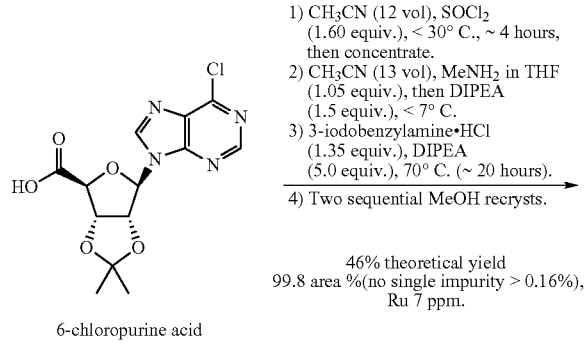

6-chloropurine acid

1) CH₃CN (12 vol), SOCl₂
(1.60 equiv.), < 30° C., ~ 4 hours,
then concentrate.
2) CH₃CN (13 vol), MeNH₂ in THF
(1.05 equiv.), then DIPEA
(1.5 equiv.), < 7° C.
3) 3-iodobenzylamine•HCl
(1.35 equiv.), DIPEA
(5.0 equiv.), 70° C. (~ 20 hours).
4) Two sequential MeOH recrysts.

46% theoretical yield
99.8 area %(no single impurity > 0.16%),
Ru 7 ppm.

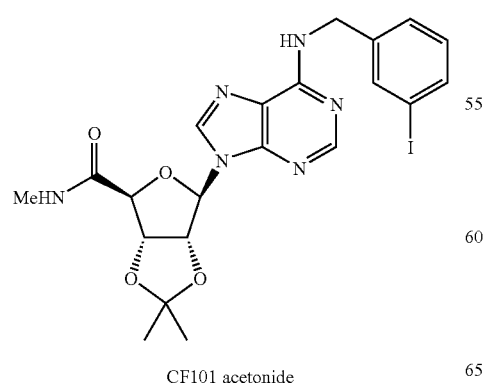

CF101 acetonide

Step D:

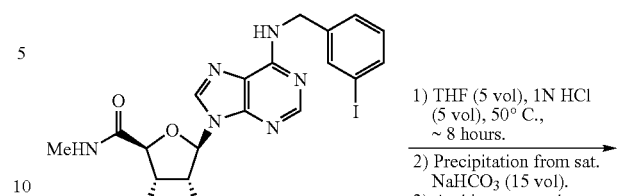

CF101 acetonide

1) THF (5 vol), 1N HCl
(5 vol), 50° C.,
~ 8 hours.
2) Precipitation from sat.
NaHCO₃ (15 vol).
3) Ambient water slurry.

91% theoretical yield
99.5 area %
(no single impurity >
0.18%),
Ru < 2 ppm.

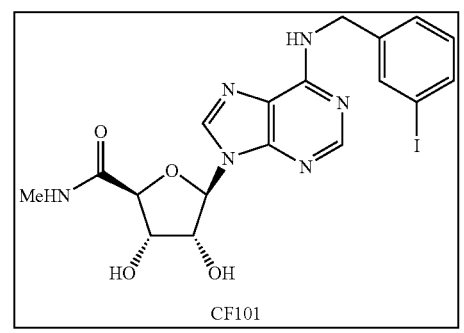

CF101

Scheme 2. Variation of the process
for the production of IB-MECA (CF101)

Step A:

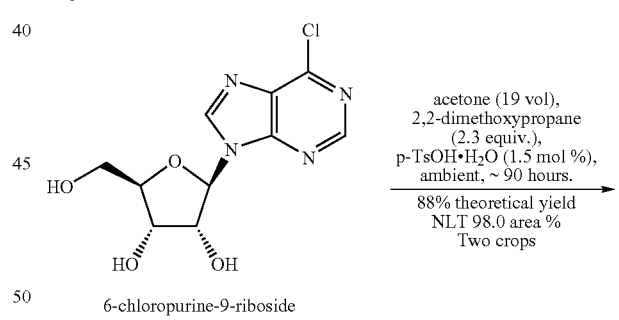

6-chloropurine-9-riboside acetone (19 vol),
2,2-dimethoxypropane
(2.3 equiv.),
p-TsOH•H₂O (1.5 mol %),
ambient, ~ 90 hours.

88% theoretical yield
NLT 98.0 area %
Two crops

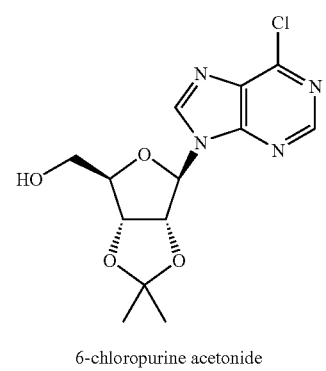

6-chloropurine acetonide

Step B:

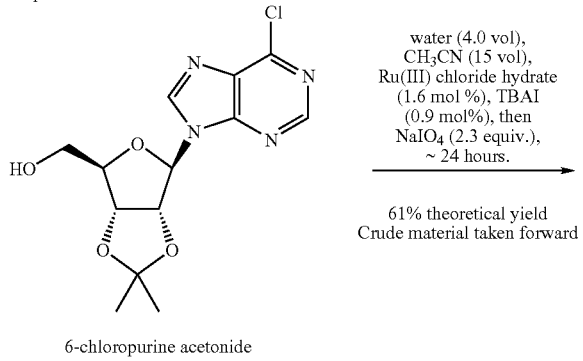

6-chloropurine acetonide 6-chloropurine acid

Step C:

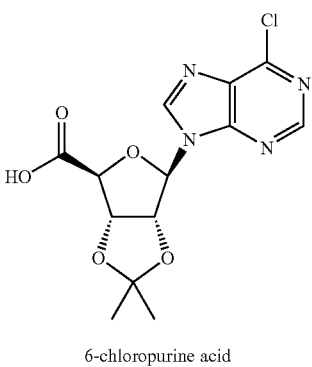

6-chloropurine acid 1) 2-propanol (15 vol)*,
3-iodobenzylamine•HCl
(1.1 equiv.), Et₃N (2.3 equiv.),
reflux, ~ 110 hours, concentrate.
2) THF (12 vol), 0-10° C., SOCl₂
(1.2 equiv.).
3) MeNH₂ in THF (4.0 equiv.),
< 15° C., 22 hours.
4) silican gel chromatography

*EtOH was initially employed.

All charges based on original
input of 6-chloropurine acetonide
and assume 100% conversion
to 6-chloropurine acid
~ 27% theoretical yield
93 area %

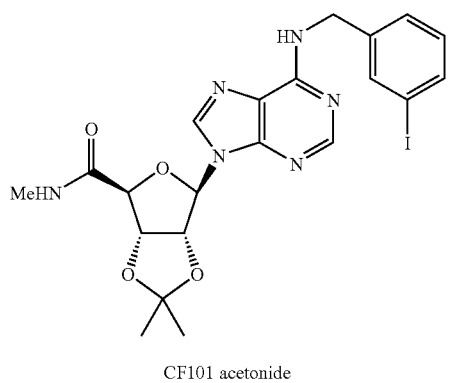

CF101 acetonide

Step D:

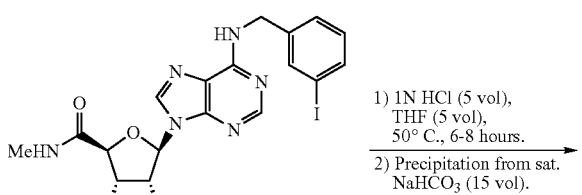

CF101 acetonide 1) 1N HCl (5 vol),
THF (5 vol),
50° C., 6-8 hours.
2) Precipitation from sat.
NaHCO₃ (15 vol).
3) Biotage purification.

47% theoretical yield
99.5 area %

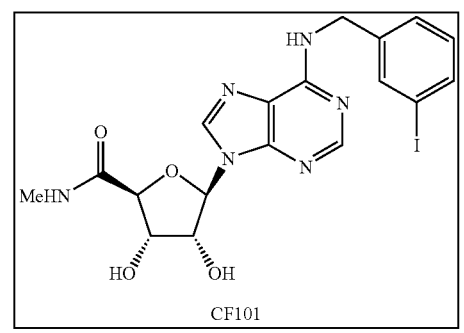

CF101

A number of key differences are noted between the processes steps of Scheme 1 and the processes steps on Scheme 2 employed for the cGMP production of M-MECA, as follows:

Step A Preparation of 6-chloropurine acetonide

In the process according to Scheme 2, the amounts added of p-TsOH.H₂O and 2,2-dimethoxypropane were increased in order to enhance the reaction rate without adversely impacting yield and quality. This cut the costly reaction-vessel residency time in half. On scale, the initial procedure was inconsistent and led to incomplete reaction. To drive the reaction to completion additional reagents had to be added in portions over a period of up three weeks, and resulted in significant increase in overall reaction volume. These charges were also optimized such that possible side-products were kept to a minimum.

The process according to Scheme 1, which is also subject of the appended claims, afforded high-quality material as a single crop in similar yield as achieved for the process of Scheme 2.

Step B Preparation of 6-chloropurine acid

According to the process detailed in Scheme 1, subsequent reagent and solvent additions in order to afford IB-MECA Acetonide were based upon the isolated weight of the acid. Whereas according to the process of Scheme 2, the addition of reagents and solvents were with respect to the weight of the isolated precursor intermediate (6-chloropurine acetonide). Thus, a slurry, an extractive IPAc/H₂O work-up, and a Na₂SO₄ drying operation were each eliminated in process of Scheme 1.

The acid in Scheme 1 was isolated from water in an easy to handle form, that can be oven dried to meet a residual water content specification (subsequent acyl chloride formation is water sensitive). A tolerable upper limit for residual water in the acid was determined to be <0.6 wt %. This was consistently met by simple vacuum oven drying, without sacrificing quality. The recovery was enhanced by increasing the washing volumes of the filter-cake, and by eliminating the aforementioned redundant processing.

Step C Preparation of IB-MECA Acetonide

There is a significant difference in the order of the three synthetic transformations (reaction with 3-iodobenzylamine, then acyl chloride formation, and finally amide formation with $MeNH_2$) between the two Schemes. The additions of reagents were optimized with respect to the input of 6-chloropurine acid (see step B above). A single reaction solvent ($CH_3CN$) was used in Scheme 1, for these reactions. This eliminated ester-impurity formation encountered when employing the processes of Scheme 2 (not shown). Additionally, according to the sequence of processes of this step in Scheme 1, the most costly material (3-iodobenzylamine) was employed in the last stage of the synthesis. The silica gel column chromatography purification requirement in the process of Scheme 2, has been replaced with MeOH recrystallizations (scheme 1). There were several other potential process impurities identified at this juncture (not shown).

Step D Preparation of IB-MECA

Biotage purification employed in the process of Scheme 2 was no longer required, since the purity of the precursor IB-MECA acetonide was improved in Scheme 1, through MeOH recrystallizations. Thermal decomposition was determined to occur during the acetonide deprotection (acidic conditions) in both Schemes, as such the reaction time is limited to 8 hours (without adversely affecting yield).

The invention claimed is:

1. A method for synthesizing IB-MECA of formula (I)

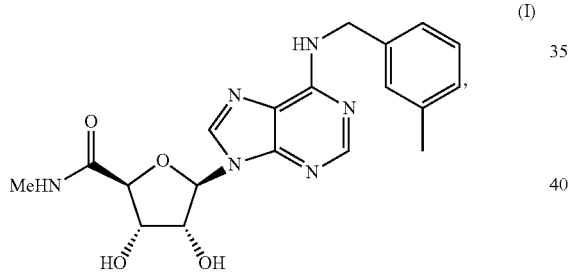

(I)

the method comprising:
reacting 6-halopurine-9-riboside of formula (II)

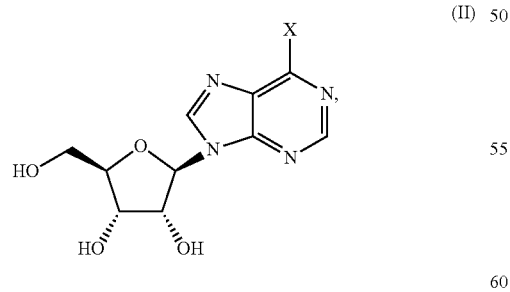

(II)

wherein X is a halogen selected from the group consisting of Cl, I and Br,
with a diol protecting reagent to obtain a reaction mixture;
diluting the reaction mixture with water and crystallizing a diol protected 6-halopurine of formula (III)

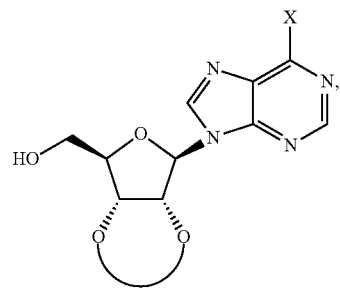

(III)

the diol protecting reagent comprising a straight or branched $C_1$-$C_6$ alkyl group;
oxidizing the primary alcohol in the diol protected 6-halopurine of formula (III), the oxidizing comprising adding a catalytic amount of an oxidizing agent comprising at least one of sodium periodate or ruthenium trichloride to obtain a second reaction mixture;
filtering the second reaction mixture;
diluting the second reaction mixture and crystallizing a respective carboxylic acid derivative of formula (IV)

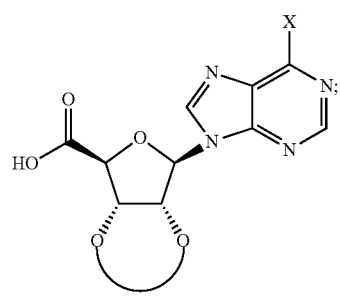

(IV)

reacting the carboxylic acid group of the derivative of formula (IV) with $SOCl_2$ to obtain an acid chloride followed by reaction with methylamine in the presence of diisopropylethylamine (DIPEA) to obtain a methylamide derivative of the diol protected 6-halopurine (III), the methylamide derivative having formula (V)

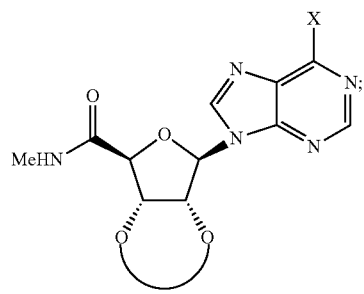

(V)

substituting the halogen group of methylamide derivative (V) with 3-iodobenzylamine, the 3-iodobenzylamine having a level of impurity less than or equal to 0.92%, in the presence of diisopropylethylamine (DIPEA) to form a diol protected IB-MECA of formula (VI)

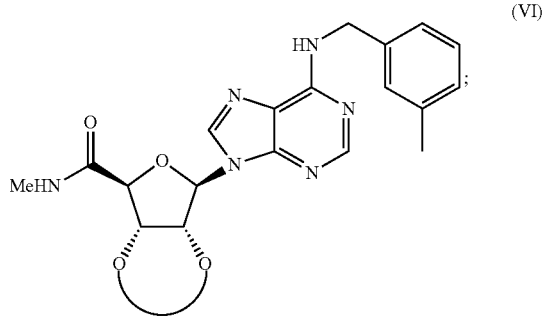 [SMILES: CNC(=O)[C@H]1O[C@@H](n2cnc3c(NCc4cccc(C)c4)ncnc32)[C@H](O)[C@@H]1O]

purifying the diol protected IB-MECA of formula (VI), the purifying comprising adding methanol and recrystallizing the diol protected IB-MECA of formula (VI),
repeating the purifying;
removing diol protection to obtain the IB-MECA of formula (I) at a purity level of greater than or equal to 99.5% and at a yield level being suitable for large scale production of the IB-MECA.

2. The method of claim 1, wherein the halogen is chloride.
3. The method of claim 1, wherein the protecting group is $C_3$-$C_6$ dialkyloxyalkane.
4. The method of claim 3, wherein the dialkyloxyalkane is 2,2-dimethoxypropane.
5. The method of claim 1, wherein the diol protection is achieved in the presence of a strong acid and a polar organic solvent.
6. The method of claim 5, wherein the strong acid is selected from p-TsOH, methane sulfonic acid, benzene sulfonic acid, formic acid, hydrochloric acid, sulfuric acid.
7. The method of claim 5, wherein the polar organic solvent is a water-miscible solvent.
8. The method of claim 7, wherein the polar organic solvent is acetone.
9. The method of claim 1, wherein the oxidizing agent comprises a mixture of ruthenium trichloride ($RuCl_3$) and sodium periodate.
10. The method of claim 1, wherein the removal of the diol protecting group is performed in the presence of a strong acid and a polar non-protic solvent.
11. The method of claim 10, wherein the strong acid is HCl and the solvent is Tetrahydrofurane (THF).
12. The method according to claim 1, wherein the method consists essentially of performing each step therein in chronological order.
13. A method for synthesizing IB-MECA of formula (I)

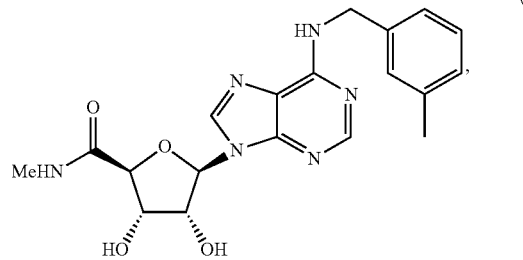

the method comprising:
reacting 6-halopurine-9-riboside of formula (II)

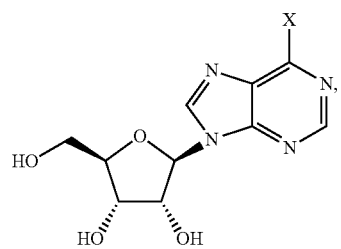

wherein X is a halogen selected from Cl, I or Br,
with a diol protecting reagent to obtain a diol protected 6-halopurine of formula (III)

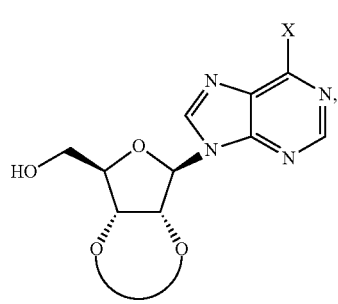

wherein the diol protecting reagent comprises a straight or branched $C_1$-$C_6$ alkyl group;
oxidizing the primary alcohol in the diol protected 6-halopurine of formula (III) by addition of a catalytic amount of an oxidizing agent comprising at least one or both of sodium periodate and ruthenium trichloride to obtain a respective carboxylic acid derivative of formula (IV)

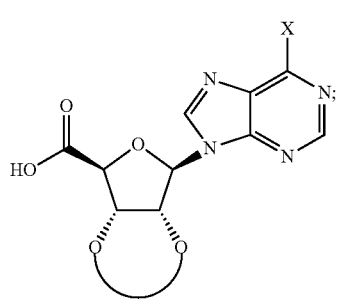

and recrystallizing the acid derivative;
reacting the carboxylic acid group of the derivative of formula (IV) with a halogenating agent selected from the group consisting of $SOCl_2$ and $PCl_5$ to obtain an acid chloride followed by reaction with methylamine in the presence of diisopropylethylamine (DIPEA) to obtain a methylamide derivative of the diol protected 6-halopurine (III), the methylamide derivative having formula (V)

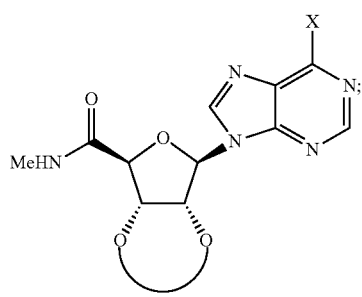 (V)

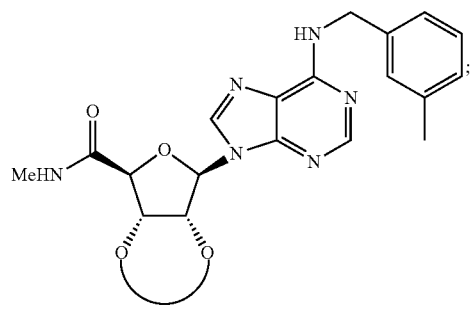 (VI)

substituting the halogen group of methylamide derivative (V) with 3-iodobenzylamine having a level of impurities below 0.92%, in the presence of diisopropylethylamine (DIPEA) to form a diol protected IB-MECA of formula (VI)

and recrystallizing the diol protected IB-MECA of formula (VI) in methanol;

removing diol protection to obtain the IB-MECA of formula (I) at a purity level over 99.5% and yield level being suitable for large scale production of the IB-MECA.

* * * * *